United States Patent
Shtarov et al.

(10) Patent No.: US 7,138,551 B2
(45) Date of Patent: Nov. 21, 2006

(54) PURIFICATION OF FLUORINATED ALCOHOLS

(75) Inventors: Alexander Borisovich Shtarov, Wilmington, DE (US); Stephen James Getty, Wilmington, DE (US); Axel Hans-Joachim Herzog, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 161 days.

(21) Appl. No.: 10/983,201

(22) Filed: Nov. 5, 2004

(65) Prior Publication Data

US 2006/0100464 A1    May 11, 2006

(51) Int. Cl.
*C07C 29/00* (2006.01)
*C07C 31/00* (2006.01)
*C07C 31/02* (2006.01)
*C07C 33/00* (2006.01)

(52) U.S. Cl. .................................. 568/840
(58) Field of Classification Search ............... 568/840
See application file for complete search history.

(56) References Cited

U.S. PATENT DOCUMENTS

| | | | |
|---|---|---|---|
| 3,532,659 | A | 10/1970 | Hager et al. |
| 5,442,097 | A | 8/1995 | Obermeier et al. |
| 5,591,877 | A | 1/1997 | Obermeier et al. |
| 5,817,284 | A | 10/1998 | Nakano et al. |
| 5,990,330 | A | 11/1999 | Sulzbach et al. |
| 6,069,291 | A | 5/2000 | Rossin et al. |
| 6,245,923 | B1 | 6/2001 | Sulzbach et al. |
| 6,563,011 | B1 | 5/2003 | Atobe et al. |
| 2001/0009652 | A1 | 7/2001 | Arno |
| 2001/0025017 | A1 | 9/2001 | Amemiya et al. |
| 2002/0131912 | A1 | 9/2002 | Tamata et al. |
| 2003/0026743 | A1 | 2/2003 | Imamura |
| 2003/0220442 | A1 | 11/2003 | Epsch et al. |
| 2004/0016343 | A1 | 1/2004 | Ferrero et al. |
| 2004/0084296 | A1 | 5/2004 | Hori et al. |

FOREIGN PATENT DOCUMENTS

| | | |
|---|---|---|
| CN | 1341478 | 3/2002 |
| EP | 0 194 690 A2 | 3/1985 |
| EP | 0 247 614 A | 2/1987 |
| EP | 0 355 787 A | 2/1990 |
| EP | 0 663 233 B1 | 8/1998 |
| EP | 1 070 728 | 1/2001 |
| EP | 0 1 070 723 A3 | 11/2003 |
| JP | 1999179201 A | 7/1999 |
| JP | 2000126598 A | 5/2000 |
| JP | 2000342931 A | 12/2000 |
| JP | 2003267900 A | 9/2002 |
| RU | 2015954 | 7/1994 |
| SU | 568 602 | 5/1977 |
| WO | WO 98/01217 | 1/1998 |
| WO | WO 2002/044297 | 6/2002 |
| WO | WO 2004/050719 | 6/2004 |

OTHER PUBLICATIONS

Brace (Journal of Fluorine Chemistry, 20 (1982) 313-327, 1981).*
Tiers, George Van Dyke: "Preparation of acyl halides and esters from salts of perfluoroalkanoic acids", Journal of Organic Chemistry, 29(7), 2038-9 Coden: Joceah; ISSN: 0022-3263, 1964, XP002381483; pp. 15-26.
Chambers R D: Reactions of Perfluoroalkanoic Acids and Derivatives: Fluorine in Organic Chemistry, 1973, pp. 211-212, XP009033576, Wiley-Interscience Publication; John Wiley & Sons, entire document.
Brace N O: "Some Approach to the Syntnesis (sic) of Fluorinated Alcohols and Esters. II. USR of F, Alkyl Iodides for the Synthesis of F-Alkyl Alkanols", Journal of Fluorine Chemistry, Elsevier, Amsterdam, NL, vol. 20, 1982, pp. 313-327, XP0000942667 ISSN: 0022-1139, p. 313. "Summary"; p. 314, first and last paragraph; p. 315, Chart I.

* cited by examiner

*Primary Examiner*—Thurman K. Page
*Assistant Examiner*—Kellette Gale

(57) ABSTRACT

A process for reducing the level of perfluoroalkanoic acids, perfluoroalkanoic esters, and perfluoroalkyliodides in fluorinated alcohols comprising heating a fluorinated alcohol, or mixtures thereof, containing said acids, esters, or iodides to a temperature of at least 175° C. in the presence of water and a base additive is disclosed.

24 Claims, No Drawings

PURIFICATION OF FLUORINATED ALCOHOLS

FIELD OF THE INVENTION

This invention relates to a process for the purification of fluorinated alcohols.

BACKGROUND OF THE INVENTION

Trace levels of perfluoroalkanoic acid impurities may occur in intermediates used in the manufacture of fluorinated alcohols. It is desirable to limit formation of these impurities in fluorinated intermediates and also during the manufacture of various polymer products using such intermediates. Furthermore, it is also desirable to eliminate or significantly reduce the occurrence in fluorinated intermediates and polymer products of potential perfluoroalkanoic acid precursors, such as their esters with 2-perfluoroalkylethyl alcohols, and perfluoroalkyliodides. Both these classes of compounds can be readily degraded by hydrolysis and/or oxidation to form perfluoroalkanoic acids.

Fluorinated alcohols are widely used as intermediates to prepare water and oil repellents, as well as soil and stain release compositions for both hard- and soft-surfaced substrates. Such substrates include building materials, such as architectural stone and tile; textiles and fabrics from natural and synthetic fibers used in apparel and carpet; as well as other surfaces. Fluorotelomer alcohols are a particular class of fluorinated alcohols used in these applications. Fluorotelomer alcohols can be prepared industrially by multiple processes that include: telomerization of pentafluoroethyliodide with tetrafluoroethylene to yield perfluoralkyliodides $F(CF_2CF_2)_nI$; reaction of these perfluoroalkyliodides with ethylene to provide 1-iodo-1H,1H,2H,2H-perfluoroalkanes having the structure $F(CF_2CF_2)_nCH_2CH_2I$; followed by hydrolysis to yield 1H,1H,2H,2H-perfluoroalkan-1-ols, $F(CF_2CF_2)_nCH_2CH_2OH$.

In U.S. patent application 2003/125421 Bladel et al. disclose a process for the recovery of highly fluorinated carboxylic acids useful as emulsifiers from fluoropolymer dispersions. Processes for the recovery of fluorinated acids from product streams do not destroy the fluorinated acids, and may leave a significant residue of the acid in the extracted liquid product.

Japan patent application 2003/267900 describes a process for the decomposition and removal of water-soluble fluorine-containing carboxylic acids, having the fluorocarbon chain interrupted by oxygen or nitrogen, when dissolved in water at temperatures of 200° C. or less in 24 hr. Perfluoroalkanoic acids (especially their more thermally stable linear isomers) and their esters are substantially more stable under these reaction conditions and are relatively insoluble in water. This process would not selectively remove perfluoroalkanoic acids, their esters and perfluoroalkyliodide impurities from fluorinated alcohols.

It is therefore desirable to develop processes that remove perfluoroalkanoic acids, their esters, and perfluoroalkyliodides from fluorinated alcohols. The present invention provides such a process.

SUMMARY OF THE INVENTION

The present invention comprises a process for selectively reducing the level of perfluoroalkanoic acids or salts thereof, perfluoroalkanoic esters, and perfluoroalkyliodides in fluorinated alcohols comprising heating a fluorinated alcohol, or mixtures thereof, containing said acids, salts, esters, and/or iodides to a temperature of at least 175° C. in the presence of water and at least one base additive.

The present invention further comprises a process for selectively reducing the level of perfluoroalkanoic acids and salts thereof in the presence of 1-iodo-1H,1H,2H,2H-perfluoroalkane comprising heating a 1-iodo-1H,1H,2H,2H-perfluoroalkane, or mixtures thereof, containing said perfluoroalkanoic acids or salts thereof to a temperature of at least 175° C. in the presence of at least one organic additive.

The present invention further comprises the products prepared by each of the above processes.

DETAILED DESCRIPTION

Hereinafter, trademarks are shown in upper case.

The terms "(meth)acrylic" and "(meth)acrylate" as used herein denote: acrylic and methacrylic; and acrylate and methacrylate, respectively.

The term "fluorinated alcohols" as used herein denotes compounds of the structure of Formula 1 or mixtures thereof:

$R_f$—$(CH_2)_m$OH          Formula 1 wherein m is 2 or 3, $R_f$ is a linear or branched $C_nF_{(2n+1)}$, and n ranges from 2 to about 20.

The term "fluorotelomer alcohols" as used herein denotes compounds of the structure of Formula 1 wherein m=2.

The term "perfluoroalkyliodides" as used herein denotes 1-iodoperfluoroalkanes of the structure of Formula 2 or mixtures thereof:

$R_f$—I          Formula 2 wherein $R_f$ is as defined above.

The term "fluorotelomer iodides" as used herein denotes compounds of the structure of Formula 3 or mixtures thereof:

$R_f$—$CH_2$—$CH_2$—I          Formula 3 wherein $R_f$ is as defined above.

The terms "perfluoroalkanoic acid" and perfluoroalkanoic acid ester" as used herein denote compounds of the structure of Formula 4, or mixtures thereof:

$R_f$—COOR          Formula 4 wherein $R_f$ is as defined above and R is H in perfluoroalkanoic acid, or R is the residue of any alcohol, including fluoroalcohols, after elimination of water during ester formation in perfluoroalkanoic acid ester.

The processes of the present invention significantly reduce the levels of specific perfluoroalkyl impurities in fluorinated alcohols. These impurities include perfluoroalkanoic acids or salts thereof, perfluoroalkyliodides, and perfluoroalkanoic acid esters of fluorotelomer alcohols; and also perfluoroalkanoic acid esters of other alcohols used as processing aids, such as isopropyl alcohol.

In a first embodiment of the present invention the process of the present invention comprises thermal treatment of fluorinated alcohols, singly or in admixture, containing impurities as noted above at a temperature above about 175° C., in the presence of water and at least one base additive. Preferably the thermal treatment is above about 185° C., and more preferably above about 195° C. Degradation of the impurities is slower at lower temperatures, and becomes less practical, especially below about 175° C. The upper temperature for the thermal treatment is about 225° C. and preferably about 215° C. Above this temperature range competing reactions may produce additional undesired impurities. The thermal treatment is carried out in the presence of water and one or more base additives. Optionally, the thermal treatment is also carried out in the presence of a hydrogen atom donor.

Water is present in the thermal treatment, preferably in the total amount of from about 5% to about 50%, preferably from about 10% to about 20%, based on the weight of fluorotelomer alcohol being treated. While the hydrolysis proceeds in the presence of higher water concentrations, the reaction volume is increased without providing any advantage. The water facilitates the hydrolysis and removal of perfluoroalkanoic acid esters and perfluoroalkyliodides. In certain cases, some water may be present in the fluorotelomer alcohol being treated, and this water content is included in calculations to determine the amount of any additional water needed for thermal treatment.

Base additives suitable for use in the practice of this invention are Brønsted bases capable of forming a salt or complex with the perfluoroalkanoic acid, including but not limited to selections from the group consisting of ammonia and its common salts such as ammonium chloride; primary, secondary, and tertiary amines and their salts; alkali metal hydroxides; and alkali metal salts, such as carbonates, bicarbonates, and acetates; and mixtures thereof. The most effective base additives are typically used at a level ranging from about 0.1% to about 5% by weight, based on the weight of the fluorotelomer alcohol. A level ranging from about 0.1% to about 2% is preferred.

The fluorinated alcohol, water, one or more base additive, and optional hydrogen donor (see below) are mixed together and agitated during heating.

Minimizing side reactions that lead to color formation during the course of thermal treatment is an advantageous aspect for controlling the quality of the finished fluorotelomer alcohols. The selection of base additive influences color formation. Color may be a result of the formation of conjugated by-products from nitrogen and sulfur compounds that are present in trace amounts. For instance, thermal treatment with ethanolamine or diethanolamine produces fluorotelomer alcohol having lighter color than does thermal treatment with stronger base such as ammonia.

At least one hydrogen atom donor, in addition to the base itself, may also be employed during the thermal treatment. These hydrogen atom donors facilitate phase transfer between organic and aqueous phase, and promote decomposition of perfluoroalkyliodides. Optional effective hydrogen donors are organic molecules containing electron-donating substituents. Preferred substituents include, but are not limited to amino-, alkoxy-, and alkyl-substituents. Suitable hydrogen atom donors are chosen from glycols, alkyl alcohols, ethers, acids, amines, salts thereof for each of the foregoing, and metal complexes thereof for each of the foregoing. Optional hydrogen donors are typically used at from 0% to about 20%, preferably from 0% to about 10%, and most preferably from 0% to about 5% by weight, based on the weight of fluorotelomer alcohol or fluorotelomer iodide material being treated. Some specific examples of effective hydrogen atom donors include, but are not limited to glycols such as ethylene glycol, 1,2-propyleneglycol, di(ethylene glycol), tri(1,2-propylene glycol), and tetraglyme; alkyl alcohols, such as 2-propanol; alkylamines such as ethanolamine, diethanolamine, triethanolamine, diethylamine, diisopropanolamine, N-ethyl-N-ethanolamine and triethylamine, and the salts of these amines; ammonia and its salts, such as ammonium chloride.

Following the thermal treatment, the base additives and optional one or more hydrogen atom donor additives are readily separated from the fluorinated alcohol by washing with water, or with water combined with dilute base or acid. Such aqueous extraction is followed by vacuum drying at about 0.5 to about 40 kPa at about 60° C. to about 100° C. Residual levels of the base additives and of hydrogen atom donors contained in the isolated fluorotelomer alcohols are sufficiently low to have no detectable effect on product quality.

The process of the present invention is used to remove perfluoroalkanoic acids or salts thereof, perfluoroalkanoic acid esters, and perfluoroalkyliodide impurities from individual fluorinated alcohols or mixtures of their homologues. The process of the present invention reduces the levels of $C_2$–$C_{20}$ perfluoroalkyl impurities. The alcohols are further used to make finished products such as polyurethanes, (meth)acrylates, phosphate esters, and other polymers.

While not wishing to be bound by theory, it is believed that under the reaction conditions most of the perfluoroalkyl radicals and/or perfluoroalkyl radical-anions abstract hydrogen atoms from a donor to form 1H-perfluoroalkanes. Perfluoroalkyl radicals are generated both by the decarboxylation of perfluoroalkanoic acids and/or salts thereof, and also by homolytic cleavage of the C—I bond of perfluoroalkyliodides. Perfluoroalkyl radical-anions are formed from perfluoroalkyliodides by single electron transfer (SET) mechanisms. Another undesirable reaction is dehydrofluorination, whereby the fluorotelomer alcohol loses hydrogen fluoride to produce the unsaturated alcohol that remains as an impurity in the fluorinated telomer alcohol (Reaction 1), Reaction 1

$F(CF_2)_nCH_2CH_2OH$ + $OH^-$ ⟶ $F(CF_2)_{(n-1)}CF\!\!=\!\!CHCH_2OH$ + $F^-$ + $H_2O$ wherein n is 2 to 20. The present invention minimizes Reaction 1 by careful selection of the treatment base reagent, such as alkylamines, ammonium or alkaline metal salts instead of alkaline metal hydroxides.

In another embodiment of the present invention, thermal treatment of fluorotelomer iodides, singly or in admixture, in the presence of at least one organic additive enables removal of perfluoroalkyliodides and perfluoroalkanoic acid and salts thereof from fluorotelomer iodides. The organic additives have electron-donating substituents. Preferred substituents are alkoxy-, alkyl-, alkenyl-, di(alkyl or aryl)amino-, or hydroxy-substituents. Organic additives suitable for use herein include glycols, alkyl alcohols, alkyl ethers, amides, tertiary amines, and salts thereof, and saturated and unsaturated hydrocarbons. The one or more organic additives are present at a level of from about 0.1% to about 20% by weight, preferably from about 0.1% to about 10%, and more preferably from about 0.1% to about 5% by weight, based on the weight of the fluorotelomer iodide. Most effective organic additives were found to work at very low loadings, less than about 5% based on the weight of the fluorotelomer iodide. Preferred organic additives have a molecular weight of from about 28 to about 1000.

The one or more organic additives are preferably water soluble and/or relatively volatile materials, which after the treatment are easily separated by contacting with an aqueous phase or by evaporation to provide the purified fluorotelomer iodides. Examples of organic additives that are easily removed by contacting with an aqueous phase are alcohols, trialkanolamines, such as triethanolamine, or polyalkylether glycols, such as polyethyleneglycols. Examples of organic additives that are easily removed by evaporation are ethylene or propylene. A particularly preferred organic additive is isopropyl alcohol. The resulting purified fluorotelomer iodides are also used to prepare fluorotelomer alcohols and other derivatives.

The thermal conditions for the treatment of fluorotelomer iodides are as described above for fluorotelomer alcohols. The thermal treatment is carried out in the presence of one or more organic additives and optional addition of water. Optionally, the thermal treatment may also include a hydrogen atom donor. The fluorotelomer iodides, singly or in admixture, are heated with the organic additive at above about 175° C., preferably above about 185° C., and more preferably above about 195° C. The upper temperature for the thermal treatment is about 225° C. and preferably about 215° C. Above this temperature range the process becomes less economically attractive and undesirable competing reactions can become significant.

The purified fluorotelomer alcohols resulting from the process of the present invention are useful for conversion into (meth)acrylate esters, polyurethane polymers, and other derivatives, containing substantially reduced concentrations of the perfluoroalkanoic acids or salts thereof, perfluoroalkanoic acid esters, and perfluoroalkyliodides. The perfluoroalkanoic acids or salts thereof, perfluoroalkanoic acid esters, and perfluoroalkyliodides are chemically converted primarily into 1H-perfluoroalkanes.

MATERIALS AND TEST METHODS

Mixture 1 comprises 1H,1H,2H,2H-perfluoroalkan-1-ols and was obtained from E. I. du Pont de Nemours and Company, Wilmington Del. Designated as Mixture 1 hereafter, the composition by weight is shown in Table 1:

TABLE 1

1H,1H,2H,2H-Perfluoroalkan-1-ol Mixture Composition.

| Chemical Name | Mixture 1 (by weight) |
| --- | --- |
| 1H,1H,2H,2H-perfluorohexan-1-ol | 0%–2% |
| 1H,1H,2H,2H-perfluorooctan-1-ol | 27%–39% |
| 1H,1H,2H,2H-perfluorodecan-1-ol | 26%–34% |
| 1H,1H,2H,2H-perfluorododecan-1-ol | 14%–20% |
| 1H,1H,2H,2H-perfluorotetradecan-1-ol | 6%–12% |
| 1H,1H,2H,2H-perfluorohexdecan-1-ol | 1%–6% |
| 1H,1H,2H,2H-perfluorooctadecan-1-ol | 0%–3% |

1-Iodo-1H,1H,2H,2H-perfluoroalkanes were obtained from E. I. du Pont de Nemours and Company, Wilmington Del. designated as Mixture 2 hereafter, the composition by weight is shown in Table 2:

TABLE 2

1-Iodo-1H,1H,2H,2H-Perfluoroalkananes Mixture Composition.

| Chemical Name | Mixture 2 (by weight) |
| --- | --- |
| 1-iodo-1H,1H,2H,2H-perfluorohexane | 0%–2% |
| 1-iodo-1H,1H,2H,2H-perfluorooctane | 27%–39% |
| 1-iodo-1H,1H,2H,2H-perfluorodecane | 26%–34% |

TABLE 2-continued

1-Iodo-1H,1H,2H,2H-Perfluoroalkananes Mixture Composition.

| Chemical Name | Mixture 2 (by weight) |
| --- | --- |
| 1-iodo-1H,1H,2H,2H-perfluorododecane | 14%–20% |
| 1-iodo-1H,1H,2H,2H-perfluorotetradecane | 6%–12% |
| 1-iodo-1H,1H,2H,2H-perfluorohexdecane | 1%–6% |
| 1-iodo-1H,1H,2H,2H-perfluorooctadecane | 0%–3% |

1H,1H,2H,2H-perfluorodecan-1-ol, perfluorooctanoic acid, perfluorooctyl iodide, and perfluorododecyl iodide are available from Syn-Quest Laboratories, Alachua, Fla.

The perfluorooctanoic acid ester of 2-perfluorooctyl-ethanol was prepared by direct esterification.

Test Method 1.

The quantitative detection (with a detection threshold 1–2 mg/kg) of perfluorooctanoic acid was performed by using a liquid chromatography tandem mass spectrometry method (liquid chromatography/mass spectrometry/mass spectrometry, LC/MS/MS). Standard solutions of perfluorooctanoic acid at known concentrations were run before and after the experimental samples to obtain calibration curve of MS integration area versus sample concentration. The measurement for each experimental sample was also verified by analyzing the sample spiked with the known amount of perfluorooctanoic acid. The level of other perfluoroalkanoic acid homologs: $C_5F_{11}COOH$ through $C_9F_{19}COOH$ was established relative to the perfluorooctanoic acid quantity in mg/kg by using liquid chromatography tandem mass spectrometry method. The identity of the peaks was verified by using corresponding perfluoroalkanoic acid standards. Additional detail of this Test method is provided in "Extraction of perfluorooctanoic acid from polytetrafluoroethylene polymers and determination by LC/MS/MS, B. S. Larsen, et al., in Abstracts of Papers, 228th ACS National Meeting, Philadelphia, Pa., United States, Aug. 22–26, 2004 (2004), FLUO-021. (American Chemical Society, Washington, D.C.).

Test Method 2.

Quantitative detection of perfluorooctyl iodide, perfluorododecyl iodide, and the perfluorooctanoic acid ester of 2-perfluorooctyl-ethanol in the starting materials as well as in final products, with detection threshold of 1–2 mg/kg, was done by gas chromatography with a mass selective detector (GC/MS). Standard solutions of these materials at known concentration were used to obtain GC/MS calibration curve prior and after the experimental samples. The measurement for each experimental sample was also verified by analyzing the sample spiked with the known amount of these material standards.

EXAMPLES

The initial levels of perfluorooctanoic acid and other impurities prior to the treatment were the combination of process impurities and optional spiking of impurities.

Example 1

1H,1H,2H,2H-perfluorodecan-1-ol (4 g, available from Syn-Quest), spiked with various impurities, ethanolamine (1.5 wt. %), and water (10 wt. %), were charged to a 5-mL stainless steel shaker tube, shaken and heated to 200° C. for 4 hours. After the separation of aqueous phase, analysis was conducted according to Test Methods 1 and 2. The level of perfluorooctanoic acid had decreased from 311 mg/kg to 12 mg/kg. The level of perfluorooctyl iodide had decreased from 161 mg/kg to less than 2 mg/kg. The level of perfluorooctanoic acid ester had decreased from 170 mg/kg to less than 2 mg/kg.

Example 2

A mixture of 1H,1H,2H,2H-perfluoroalkan-1-ols, 4.5 g (Mixture 1, average MW=481, spiked with perfluorododecyl iodide), diethanolamine (1.7 wt. %), and water (11 wt. %), were charged in a 5-mL stainless steel shaker tube and heated to 200° C. for 4 hours. After the separation of aqueous phase, analysis was conducted according to Test Method 2. The level of perfluorododecyl iodide in the mixture of 1H,1H,2H,2H-perfluoroalkan-1-ols had decreased from 188 mg/kg to 3 mg/kg.

Example 3

A mixture of 1H,1H,2H,2H-perfluoroalkan-1-ols, 280 g (Mixture 1, 0.582 mol, average MW=481), ethanolamine $NH_2CH_2CH_2OH$ (4.2 g, 0.069 mol, 1.5 wt. %), water (28 g, 10 wt. %), and isopropyl alcohol, MW=60 (14 g, 5 wt. %), were charged to a 400-mL stainless steel shaker tube, shaken and heated to 200° C. for 4 hours. Perfluorooctyl iodide (190 mg/kg), and perfluorooctanoic acid ester (80 mg/kg). After the separation of aqueous phase after the treatment, analyses were conducted according to Test Methods 1 and 2. The level of perfluorooctanoic acid had decreased from 100 mg/kg to 6 mg/kg. The level of perfluorooctyl iodide had decreased from 190 mg/kg to less than 2 mg/kg. The level of perfluorooctanoic acid ester had decreased from 80 mg/kg to less than 2 mg/kg.

Example 4

A mixture of 1H,1H,2H,2H-perfluoroalkan-1-ols, 450 g (Mixture 1, 0.936 mol, average MW=481), ethanolamine (6.75 g, 1.5 wt. %), and water (45 g, 10 wt. %), were charged to a 400-mL stainless steel shaker tube, shaken and heated to 200° C. for 4 hours. After the separation of aqueous phase, analyses were conducted according to Test Methods 1 and 2. The level of perfluorooctanoic acid had decreased from 100 mg/kg to 4 mg/kg. The level of perfluorooctyl iodide had decreased from 190 mg/kg to less than 2 mg/kg. The level of perfluorooctanoic acid ester had decreased from 80 mg/kg to less than 2 mg/kg.

Example 5

A mixture of 1H,1H,2H,2H-perfluoroalkan-1-ols, 4.17 g (Mixture 1, average MW=481), diethanolamine $NH(CH_2CH_2OH)_2$ (0.09 g, 2.1 wt. %), water (0.2 g, 4.9 wt. %), were charged in a 5-mL stainless steel shaker tube and heated to 195° C. for 4 hours. After the separation of aqueous phase, analyses were conducted according to Test Methods 1 and 2. The level of perfluorooctanoic acid in the mixture of 1H,1H,2H,2H-perfluoroalkan-1-ols had decreased from 80 mg/kg to 4 mg/kg. The final level of $C_5F_{11}COOH$ was 5–8 mg/kg, $C_6F_{13}COOH$ was less than 4 mg/kg, $C_8F_{17}COOH$ and $C_9F_{19}COOH$ were below detection. The level of perfluorooctyl iodide had decreased from 90 mg/kg to less than 2 mg/kg.

Example 6

Mixture of 1-iodo-1H,1H,2H,2H-perfluoroalkanes, 250 g (Mixture 2, average MW=591), and isopropanol (5 wt. %) were charged in a 400-mL Inconell shaker tube and heated to 190° C. for 12 hours. Analyses were conducted according to Test Methods 1 and 2. The level of perfluorooctyl iodide had decreased from 320 to 14 mg/kg and the level of perfluorooctanoic acid decreased from 45 to 2 mg/kg.

Example 7

Mixture of 1-iodo-1H,1H,2H,2H-perfluoroalkanes, 450 g (Mixture 2, average MW=591), and monomethoxy-polyethyleneglycol (MW=350, 0.75 wt. %) were charged in a 400-mL stainless steel shaker tube and heated to 195° C. for 4 hours. Analyses were conducted according to Test Methods 1 and 2. The level of perfluorooctyl iodide had decreased from 320 to 23 mg/kg and the level of perfluorooctanoic acid decreased from 45 to 12 mg/kg.

Examples 8–18

A mixture of 1H,1H,2H,2H-perfluoroalkan-1-ols, (3–5 g, Mixture 1, average MW=481 for Examples 8–18) combined with the additives in the amounts listed in Table 3 as weight percent of Mixture 1, were charged to a shaker tube and heated to the temperature designated in Table 3 for the time listed. After separation, analyses were conducted according to Test Methods 1 and 2. The starting and final levels of impurities were as listed in Table 3.

TABLE 3

| Ex. # | Temp, time | Additives* | Impurities: starting/final (mg/kg) | | |
|---|---|---|---|---|---|
| | | | $C_7F_{15}$—$CO_2H$ | $C_8F_{17}I$ | $C_7F_{15}CO_2$—$CH_2CH_2C_8F_{17}$ |
| 8 | 200° C., 4 h | DEA (3%), Water (10%) | 100/5 | 190/ND | 82/ND |
| 9 | 195° C., 4 h | DEA (0.25%), Water (10%) | 100/5 | 174/ND | 78/ND |
| 10 | 195° C., 4 h | None | 100/5 | 174/70 | 78/56 |
| 11 | 195° C., 4 h | Water (10%) | 80/20 | 90/31 | 80/50 |
| 12 | 200° C., 4 h | EA (1.5%), Water (11%) | 100/5 | 174/ND | 80/ND |
| 13 | 200° C., 4 h | DEA-HCl (1.1%), Water (10%) | 100/3 | 174/ND | 80/ND |

TABLE 3-continued

| Ex. # | Temp, time | Additives* | Impurities: starting/final (mg/kg) | | |
|---|---|---|---|---|---|
| | | | $C_7F_{15}$—$CO_2H$ | $C_8F_{17}I$ | $C_7F_{15}CO_2$—$CH_2CH_2C_8F_{17}$ |
| 14 | 200° C., 4 h | LiOH—H2O (1%), Water (10%), IPA (5%) | 100/10 | 174/ND | 80/ND |
| 15 | 205° C., 4 h | PEG-200 (1.4%) Water (10%) | 80/8 | 90/ND | |
| 16 | 205° C., 4 h | DEA (2%), Titanate A (0.4%), Water 14% | 80/5 | 90/2 | |
| 17 | 200° C., 4 h | NH(iPr)₂ (1.5%), Water (10%) | 100/30 | 190/ND | 82/ND |
| 18 | 200° C., 4 h | DEA (1.9%), Tripropyleneglycol (2%), Water 5% | 80/4 | 90/ND | |

*For examples 8–18 the amount of additives as wt. % of Mixture 1.

Titanate A is 80% titanium (IV) (triethanolamineaminato) isopropoxide and 20% isopropyl alcohol, obtained from E. I. du Pont de Nemours and Company, Wilmington Del.;
DEA=diethanolamine;
EA=ethanolamine;
PEG-200=polyethyleneglycol with average MW=200;
IPA=isopropyl alcohol;
iPr=isopropyl;
ND=not detectable, detection limits 1–2 mg/kg, see Test Methods 1 and 2.

What is claimed is:

1. A process for selectively reducing the level of perfluoroalkanoic acids or salts thereof, perfluroalkanoic esters, and perfluoroalkyliodides in fluorinated alcohols comprising heating a fluorinated alcohol, or mixtures thereof, containing said acids, salts, esters, or iodides to a temperature of at least about 175° C. in the presence of water and at least one base additive.

2. The process of claim 1 wherein the fluorinated alcohol is of formula $R_f(CH_2)_mOH$ wherein $R_f$ is —$C_nF_{(2n+1)}$, n is 2 to about 20, or a mixture thereof, and m is 2 to 3.

3. The process of claim 1 wherein the base is a Brønsted base.

4. The process of claim 1 wherein the base additive is selected from the group consisting of ammonia, ammonia salts, primary amines, secondary amines, tertiary amine, amine salts, alkali metal hydroxides, alkali metal salts, and mixtures thereof.

5. The process of claim 4 wherein the base additive or mixture of base additives is present at a level of from about 0.1% to about 20% by weight of the fluorinated alcohol.

6. The process of claim 1 further comprising heating in the presence of at least one additional hydrogen atom donor.

7. The process of claim 6 wherein the hydrogen atom donor is an organic molecule containing electron-donating substituents.

8. The process of claim 6 wherein the hydrogen atom donor is selected from the group consisting of glycols, alkyl alcohols, ethers, acids, amines, salts thereof for each of the foregoing, and complexes with metals thereof for each of the foregoing.

9. The process of claim 6 wherein the hydrogen atom donor is present at a level of 0 to about 20% by weight of the fluorinated alcohol.

10. The process of claim 1 wherein the fluorinated alcohol and base additive are agitated during heating.

11. The process of claim 1 further comprising separation of the fluorinated alcohol.

12. The process of claim 1 or 6 wherein color formation is minimized by selection of the base additives.

13. The process of claim 1 or 6 wherein the heating is at a temperature of from about 175° C. to about 225° C.

14. A process for selectively reducing the level of perfluoroalkanoic acids and salts thereof, and perfluoroalkyliodides in the presence of 1-iodo-1H,1H,2H, 2H-perfluoroalkane comprising heating a 1-iodo-1H,1H,2H,2H-perfluoroalkane, or mixtures thereof, containing said perfluoroalkanoic acids or salts thereof to a temperature of at least 175° C. in the presence of at least one organic additive.

15. The process of claim 14 wherein the 1-iodo-1H,1H,2H,2H-perfluroalkane is of formula $R_fCH_2CH_2I$ wherein $R_f$ is —$C_nF_{(2n+1)}$ wherein n is 2 to about 20.

16. The process of claim 14 wherein the organic additive is a compound having electron-donating substituents.

17. The process of claim 14 wherein the organic additive is selected from the group consisting of glycols, alkyl alcohols, alkyl ethers, amides, tertiary amines, salts thereof, saturated and unsaturated hydrocarbons.

18. The process of claim 14 wherein the organic additive has a molecular weight from about 28 to about 1000.

19. The process of claim 14 wherein the organic additive is isopropyl alcohol.

20. The process of claim 14 wherein the organic additive or mixture of organic additives is present at a level of 0.1% to about 20% by weight of the 1-iodo-1H,1H,2H,2H-perfluoroalkane.

21. The process of claim 14 wherein the heating is at a temperature of from about 175° C. to about 225° C.

22. The process of claim 14 further comprising heating in the presence of water.

23. The process of claim 14 wherein the perfluoroalkanoic acids, salts thereof, perfluoroalkyliodides, 1-iodo-1H,1H,2H,2H-perfluoroalkane, and organic additive are agitated during heating.

24. The process of claim 14 further comprising separation of the 1-iodo-1H,1H,2H,2H-perfluoroalkane.

* * * * *

UNITED STATES PATENT AND TRADEMARK OFFICE
CERTIFICATE OF CORRECTION

PATENT NO. : 7,138,551 B2 Page 1 of 1
APPLICATION NO. : 10/983201
DATED : November 21, 2006
INVENTOR(S) : Shtarov Alexander Borisovich et al.

It is certified that error appears in the above-identified patent and that said Letters Patent is hereby corrected as shown below:

Claim 4, column 9, line 44, delete "amine" and substitute therefor -- amines -- .

Signed and Sealed this

Twenty-seventh Day of November, 2007

JON W. DUDAS
*Director of the United States Patent and Trademark Office*